US011974975B2

(12) United States Patent
Gut et al.

(10) Patent No.: US 11,974,975 B2
(45) Date of Patent: May 7, 2024

(54) COMPOSITIONS AND METHODS USING AT LEAST ONE GLYCINE OR DERIVATIVE THEREOF, AT LEAST ONE N-ACETYLCYSTEINE OR DERIVATIVE THEREOF, AND AT LEAST ONE NICOTINAMIDE RIBOSIDE OR NAD+ PRECURSOR

(71) Applicant: SOCIETE DES PRODUITS NESTLE S.A., Vevey (CH)

(72) Inventors: Philipp Gut, Geneva (CH); Stephanie Blum-Sperisen, Pully (CH); Giulia Lizzo, Echandens (CH)

(73) Assignee: Societe des Produits Nestle S.A., Vevey (CH)

( * ) Notice: Subject to any disclaimer, the term of this patent is extended or adjusted under 35 U.S.C. 154(b) by 201 days.

(21) Appl. No.: 17/280,308

(22) PCT Filed: Sep. 26, 2019

(86) PCT No.: PCT/EP2019/076075
§ 371 (c)(1),
(2) Date: Mar. 26, 2021

(87) PCT Pub. No.: WO2020/064946
PCT Pub. Date: Apr. 2, 2020

(65) Prior Publication Data
US 2022/0000820 A1    Jan. 6, 2022

Related U.S. Application Data

(60) Provisional application No. 62/737,189, filed on Sep. 27, 2018.

(51) Int. Cl.
*A01N 43/04*    (2006.01)
*A23L 33/175*   (2016.01)
*A61K 31/198*   (2006.01)
*A61K 31/70*    (2006.01)
*A61K 31/706*   (2006.01)
*A61K 45/06*    (2006.01)

(52) U.S. Cl.
CPC .......... *A61K 31/198* (2013.01); *A23L 33/175* (2016.08); *A61K 31/706* (2013.01); *A61K 45/06* (2013.01)

(58) Field of Classification Search
None
See application file for complete search history.

(56) References Cited

U.S. PATENT DOCUMENTS

| 6,103,756 | A  | 8/2000  | Gorsek      |
|-----------|----|---------|-------------|
| 2007/0116779 | A1 | 5/2007  | Mazzio      |
| 2007/0248690 | A1 | 10/2007 | Trager      |
| 2007/0286909 | A1 | 12/2007 | Smith et al.|
| 2010/0227812 | A1 | 9/2010  | Haley et al.|
| 2011/0034519 | A1 | 2/2011  | McCord      |
| 2014/0288177 | A1 | 9/2014  | Sekhar      |
| 2015/0209306 | A1 | 7/2015  | Bredesen et al.|
| 2016/0302451 | A1 | 10/2016 | Hudnall     |
| 2017/0290768 | A1 | 10/2017 | Barzilay et al.|
| 2018/0221397 | A1 | 8/2018  | Duronio     |

FOREIGN PATENT DOCUMENTS

| CN | 107115332   | 9/2017  |
| WO | 2016191468  | 12/2016 |
| WO | 2017109195  | 6/2017  |
| WO | 2018117954  | 6/2018  |

OTHER PUBLICATIONS

Merriam-Webster. (n.d.). Reduce. In Merriam-Webster.com dictionary. Retrieved Mar. 3, 2023, from https://www.merriam-webster.com/dictionary/reduce.*
Wessner, B., et al. "Effect of single and combined supply of glutamine, glycine, N-acetylcysteine, and R, S-α-lipoic acid on glutathione content of myelomonocytic cells." Clinical Nutrition 22.6 (2003): 515-522.*
Mardinoglu et al. "Personal model-assisted identification of NAD+ and glutathione metabolism as intervention target in NAFLD" Molecular Systems Biology, 2017, vol. 13, No. 3, pp. 1-17.
Steininger et al. "Infusion of Dipeptides as Nutritional Substrates for Glutamine, Tyrosine, and Branched-Chain Amino Acids in Patients With Acute Pancreatitis" Metabolism, Aug. 1989, vol. 38, No. 8, suppl. 1, pp. 78-81.
Mardinoglu et al. "Systems biology in hepatology: approaches and applications" Nature Reviews / Gastroenterology & Hepatology, Jun. 2018, vol. 15, pp. 365-377.
Fitzgerald, Kara "Three amino acids walk into a bar . . . the adventures of supporting glutathione synthesis in fatty liver disease using serine & nicotinamide riboside" Dr. Kara Fitzgerald—Functional Medicine, Sep. 11, 2018, pp. 1-6, retrieved from the Internet at URL:https://www.drkarafitzgerald.com/2018/09/11/three-amino-acids-walk-into-a-bar-the-adventures-of-supporting-glutathione-synthesis-in-fatty-liver-disease-using-serine-nicotinamide-riboside/.

(Continued)

*Primary Examiner* — Patrick T Lewis
(74) *Attorney, Agent, or Firm* — K&L Gates LLP

(57) ABSTRACT

A composition can treat or prevent at least one physical state selected from the group consisting of oxidative stress, a condition associated with oxidative stress, a reduced level of glutathione, and a condition associated with a reduced level of glutathione. The composition contains an effective amount of a combination of at least one glycine or functional derivative thereof, at least one N-acetylcysteine or functional derivative thereof, and at least one nicotinamide riboside or NAD+ precursor. The composition can be orally administered, for example as one or more of a food product, a food for special medical purposes (FSMP), a nutritional supplement, a ready to drink formula, a dairy-based drink, a low-volume liquid supplement, powder formats for liquid reconstitution or a meal replacement beverage.

19 Claims, 1 Drawing Sheet

(56) References Cited

OTHER PUBLICATIONS

Chinese Office Action for Appl No. 201980058493.5 dated May 6, 2023.
Castilho et al. "Oxidative Stress, Mitochondrial Function, and Acute Glutamate Excitotoxicity in Cultured Cerebellar Granule Cells", Journal of Neurochemistry, vol. 72, Issue No. 4, 1999, pp. 1394-1401.
Rolo et al., "Diabetes and Mitochondrial Function: Role of Hyperglycemia and Oxidative Stress", Toxicology and Applied Pharmacology, vol. 212, Issue No. 2, 2006, pp. 167-178.
Bhat et al., "Oxidative Stress, Mitochondrial Dysfunction and Neurodegenerative Diseases; a Mechanistic Insight", Biomedicine & Pharmacotherapy, vol. 74, 2015, pp. 101-110.
Cui et al., "Oxidative Stress, Mitochondrial Dysfunction, and Aging", Journal of Signal Transduction, vol. 2012, 2012, pp. 1-13.
Kalinchenko et al., "Sarcopenia: Epidemiology, Etiopathogenesis, Clinical Picture, Diagnosis, Treatment", Effective Pharmacotherapy, vol. 27, 2015, pp. 56-65.
Khodos et al., "Oxidatiive Stress and its Role in Pathogenesis", The General Pathology and Pathological Physiology, vol. 14, Issue No. 4, 2017, pp. 381-398.
Todorov et al., "Mitochondria: Oxidative Stress and Mitochondrial DNA Mutations in the Development of Pathology, the Aging Process, and Apoptosis", Russian Chemical Journal, vol. 51, Issue No. 1, 2007, pp. 93-106.
Office Action Received for Russian Application No. 2021111065, mailed on Jul. 13, 2023, 12 Pages (Official Copy Only).

\* cited by examiner

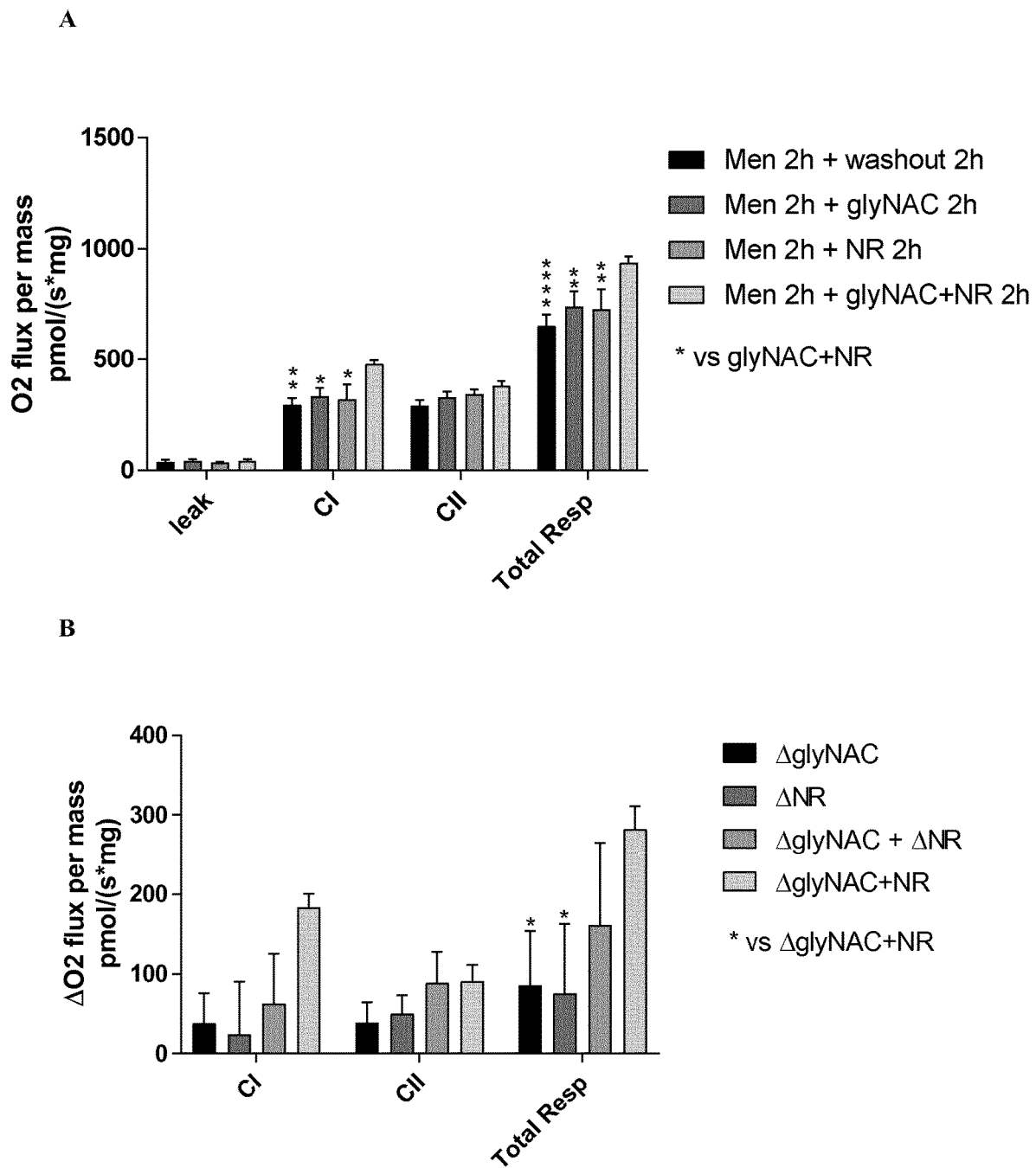

COMPOSITIONS AND METHODS USING AT LEAST ONE GLYCINE OR DERIVATIVE THEREOF, AT LEAST ONE N-ACETYLCYSTEINE OR DERIVATIVE THEREOF, AND AT LEAST ONE NICOTINAMIDE RIBOSIDE OR NAD$^+$ PRECURSOR

CROSS REFERENCE TO RELATED APPLICATIONS

The present application is a National Stage of International Application No. PCT/EP2019/076075, filed on Sep. 26, 2019, which claims priority to U.S. Provisional Patent Application No. 62/737,189, filed on Sep. 27, 2018, the entire contents of which are being incorporated herein by reference.

BACKGROUND

The present disclosure generally relates to compositions and methods that can treat or prevent oxidative stress, a condition associated with oxidative stress, a reduced level of glutathione, or a condition associated with a reduced level of glutathione. Alternatively or additionally, the compositions and the methods can improve exercise capacity and physical function.

Population aging has been a remarkable demographic event. As the growth of the older population has outpaced the total population due to increased longevity, the proportion of older persons relative to the rest of the population has increased considerably. For example, one in every twelve individuals was at least 60 years of age in 1950, and one in every ten was aged 60 years or older by the end of 2000. By the end of 2050, the number of persons worldwide that is 60 years or over is projected to be one in every five.

Aged or aging individuals frequently suffer some degree of cognitive impairment, including decline in cognitive function, that progresses with age, and age-related changes in brain morphology and cerebrovascular function are commonly observed. Cognitive decline has been consistently reported with aging across a range of cognitive domains including processing speed, attention, episodic memory, spatial ability and executive function. Brain imaging studies have revealed that these normal age-related cognitive declines are associated with decreases in both grey and white matter volume in the brain, with the fronto-striatal system most heavily compromised with aging. These decreases in cortical volume can be attributed to a number of detrimental cellular processes involved with normal aging, such as accumulation of damage by free radicals over time leading to oxidative damage, chronic low-grade inflammation, homocysteine accumulation (which when elevated are a risk factor for cognitive impairment and dementia), and decreased mitochondrial efficiency. In addition to direct cellular damage, the brain is also indirectly impaired by insults to micro-vascular structures. It is evident that the pathology of aging and also dementia involves a complexity of these interacting factors which are linked together. For example, mitochondrial dysfunction leads to increased oxidative stress, and oxidative stress can trigger inflammation and vascular insults.

Furthermore, cognitive decline is an early predictor or Alzheimer pathology and begins before the onset of dementia. In this context, the cognitive composite score represents a reliable means to assess the cognitive decline preceding dementia. Considerable evidence suggests that maintaining brain health and preventing cognitive decline with advancing age may prevent or delay development of dementia due to Alzheimer's disease and other aged related neuropathologies.

In biology and psychology, the term "stress" refers to the consequence of the failure of a human or other animal to respond appropriately to physiological, emotional, or physical threats, whether actual or imagined. The psychobiological features of stress may present as manifestations of oxidative stress, i.e., an imbalance between the production and manifestation of reactive oxygen species and the ability of a biological system readily to detoxify the reactive intermediates or to repair the resulting damage. Disturbances in the normal redox state of tissues can cause toxic effects through the production of peroxides and free radicals that damage all of the components of the cell, including proteins, lipids, and DNA. Some reactive oxidative species can even act as messengers through a phenomenon called "redox signaling."

In humans, oxidative stress is involved in many diseases. Examples include atherosclerosis, Parkinson's disease, heart failure, myocardial infarction, Alzheimer's disease, schizophrenia, bipolar disorder, fragile X syndrome, and chronic fatigue syndrome.

One source of reactive oxygen under normal conditions in humans is the leakage of activated oxygen from mitochondria during oxidative phosphorylation. Other enzymes capable of producing superoxide (O2−) are xanthine oxidase, NADPH oxidases and cytochromes P450. Hydrogen peroxide, another strong oxidizing agent, is produced by a wide variety of enzymes including several oxidases. Reactive oxygen species play important roles in cell signaling, a process termed redox signaling. Thus, to maintain proper cellular homeostasis a balance must be struck between reactive oxygen production and consumption.

Oxidative stress contributes to tissue injury following irradiation and hyperoxia. It is suspected to be important in neurodegenerative diseases, including Alzheimer's disease, Parkinson's disease, amyotrophic lateral sclerosis (ALS), and Huntington's disease.

Oxidative stress is also thought to be linked to certain cardiovascular diseases, since oxidation of low-density lipoprotein (LDL) in the vascular endothelium is a precursor to plaque formation. Oxidative stress also plays a role in the ischemic cascade due to oxygen reperfusion injury following hypoxia. This cascade includes both strokes and heart attacks. Oxidative stress has also been implicated in chronic fatigue syndrome.

Moreover, the free radical theory of aging suggests that the biological process of aging results in increased oxidative stress in elderly humans. The ability of a cell to resist the damaging potential of oxidative stress is determined by a vital balance between generation of oxidant free radicals and the defensive array of antioxidants available to the cell. There are multiple antioxidant defense systems and of these, glutathione (GSH) is the most abundant intracellular component of overall antioxidant defenses. GSH, a tripeptide, is synthesized from precursor amino-acids glutamate, cysteine, and glycine in two steps catalyzed by glutamate cysteine ligase (GCL, also known as gamma-glutamylcysteine synthetase, EC 6.3.2.2) and gamma-L-glutamyl-L-cysteine:glycine ligase (also known as glutathione synthetase, EC 6.3.2.3), and GSH synthesis occurs de novo in cells.

Nicotinamide riboside can promote the increase of intracellular levels of nicotinamide adenine dinucleotide (NAD$^+$) in cells and tissues for improving cell and tissue survival. Moreover, the combination of glycine and N-acetylcysteine (NAC) can be utilized for therapeutic and/or preventative indications in mammals in need thereof. For example, the combination of glycine and N-acetylcysteine (NAC) can provide beneficial effects with respect to impaired glutathione turnover and/or increased oxidative stress and/or oxidant damage in a mammal, including such impaired glutathione turnover and/or increased oxidative stress and/or oxidant damage in aging or diabetes, and can be combined with nicotinamide riboside.

Further regarding $NAD^+$ which can be increased intracellularly using the disclosures herein (e.g., by the combination of glycine and NAC), all living cells utilize pathways involving NAD, and NAD+ is the oxidized form of NAD. In metabolism, NAD is involved in redox reactions, carrying electrons from one reaction to another. NAD+ accepts electrons from other molecules and becomes reduced to form NADH, which can then be used as a reducing agent to donate electrons. These electron transfer reactions are the main function of NAD, but it is also used in other cellular processes, most notably a substrate of enzymes that add or remove chemical groups from proteins in posttranslational modifications.

SUMMARY

The different combinations of compounds disclosed herein reduce oxidative stress and improve mitochondrial function (both of which are mechanistically linked). Mitochondrial dysfunction contributes to cellular damage, partially through reactive oxygen species (ROS) and metabolic derangements (by not being able to metabolize nutrients), in turn leading to metabolic and degenerative diseases. Without being bound by theory, the present inventors believe that the different combinations of compounds disclosed herein, by reducing oxidative stress and improving mitochondrial function, can treat, reduce incidence of, or reduce severity of such metabolic and degenerative diseases at least with a combined effect, possibly potentiating each other or providing synergy.

Accordingly, in a general embodiment, the present disclosure provides a method of treating or preventing at least one physical state selected from the group consisting of oxidative stress, a condition associated with oxidative stress, a reduced level of glutathione, and a condition associated with a reduced level of glutathione. The method comprises administering to an individual in need thereof an effective amount of a combination of at least one glycine or functional derivative thereof, at least one N-acetylcysteine or functional derivative thereof, and at least one nicotinamide riboside or $NAD^+$ precursor.

In an embodiment, the method comprises administering to an individual in need thereof an effective amount of a combination of at least one glycine or functional derivative thereof and at least one nicotinamide riboside or $NAD^+$ precursor.

In an embodiment, the method comprises administering to an individual in need thereof an effective amount of a combination of at least one N-acetylcysteine or functional derivative thereof, and at least one nicotinamide riboside or $NAD^+$ precursor.

In an embodiment, the at least one physical state is selected from the group consisting of deleterious effects of aging, muscle loss, pre-diabetes, gestational diabetes, type I diabetes, type II diabetes, complications from diabetes, insulin resistance, metabolic syndrome, dyslipidemia, overweight, obesity, raised cholesterol levels, raised triglyceride levels, elevated fatty acid levels, fatty liver disease, renal disease, cardiovascular disease, neurodegenerative disease, impaired cognitive function, myopathy such as statin-induced myopathy, non-alcoholic steatohepatitis, tinnitus, dizziness, alcohol hangover, hearing impairment, osteoporosis, hypertension, atherosclerosis/coronary artery disease, myocardial damage after stress, traumatic brain injury, cystic fibrosis, inflammation, cancer, and HIV infection.

In an embodiment, the at least one glycine or functional derivative thereof is selected from the group consisting of L-glycine, L-glycine ethyl ester, D-Allylglycine; N-[Bis(methylthio)methylene]glycine methyl ester; Boc-allyl-Gly-OH (dicyclohexylammonium) salt; Boc-D-Chg-OH; Boc-Chg-OH; (R)-N-Boc-(2'-chlorophenyl)glycine; Boc-L-cyclopropylglycine; Boc-L-cyclopropylglycine; (R)-N-Boc-4-fluorophenylglycine; Boc-D-propargylglycine; Boc-(S)-3-thienylglycine; Boc-(R)-3-thienylglycine; D-a-Cyclohexylglycine; L-a-Cyclopropylglycine; N-(2-fluorophenyl)-N-(methylsulfonyl)glycine; N-(4-fluorophenyl)-N-(methylsulfonyl)glycine; Fmoc-N-(2,4-dimethoxybenzyl)-Gly-OH; N-(2-Furoyl)glycine; L-a-Neopentylglycine; D-Propargylglycine; sarcosine; Z-a-Phosphonoglycine trimethyl ester, and mixtures thereof.

In an embodiment, the combination is administered orally.

In an embodiment, the combination is administered in a composition selected from the group consisting of a food product, a food for special medical purposes (FSMP), a nutritional supplement, a ready to drink formula, a dairy-based drink, a low-volume liquid supplement, powder formats for liquid reconstitution, a meal replacement beverage, and combinations thereof.

In an embodiment, the combination is administered in a composition that comprises a dipeptide that provides at least a portion of the at least one glycine or functional derivative thereof and the at least one N-acetylcysteine or functional derivative thereof.

In an embodiment, the at least one glycine or functional derivative thereof, the at least one N-acetylcysteine or functional derivative thereof, and the at least one nicotinamide riboside or $NAD^+$ precursor are administered in the same composition.

In an embodiment, one or more of the at least one glycine or functional derivative thereof, the at least one N-acetylcysteine or functional derivative thereof, and the at least one nicotinamide riboside or $NAD^+$ precursor are administered in a different composition relative to the remainder of the combination.

In another embodiment, the present disclosure provides a method of delaying off-set of metabolic decline, maintaining muscle mass, decreasing oxidative stress, maintaining immune function and/or maintaining cognitive function in a healthy older adult. The method comprises administering to the healthy older adult an effective amount of a combination of at least one glycine or functional derivative thereof, at least one N-acetylcysteine or functional derivative thereof, and at least one nicotinamide riboside or $NAD^+$ precursor. The healthy older adult can be elderly.

In another embodiment, the present disclosure provides a method of enhancing metabolizing of reactive oxygen species, improving glucose control and/or improving muscle function in an individual with at least one of obesity, pre-diabetes or diabetes. The method comprises administering to the individual an effective amount of a combination of at least one glycine or functional derivative thereof, at least one N-acetylcysteine or functional derivative thereof, and at least one nicotinamide riboside or $NAD^+$ precursor.

In another embodiment, the present disclosure provides a method of improving mitochondrial function in an individual with sarcopenia. The method comprises administering to the individual an effective amount of a combination of at least one glycine or functional derivative thereof, at least one N-acetylcysteine or functional derivative thereof, and at least one nicotinamide riboside or NAD$^+$ precursor. The individual with sarcopenia can be otherwise healthy.

In another embodiment, the present disclosure provides a method of improving one or more of fetal metabolic programming for prevention of later development of obesity, pre-diabetes and/or diabetes, maternal and fetal health in gestational diabetes, exercise capacity and physical function, quality of life, longevity, memory, cognition, post-traumatic recovery and survival, or recovery from trauma and surgery. The method comprises administering to an individual an effective amount of a combination of at least one glycine or functional derivative thereof, at least one N-acetylcysteine or functional derivative thereof, and at least one nicotinamide riboside or NAD$^+$ precursor. The individual can have at least one of impaired cognitive function or a cognitive disorder, and the composition can comprise an amount of the combination effective to improve cognition. The individual can not have impaired cognitive function or a cognitive disorder, and the composition can comprise an amount of the combination effective to improve cognition.

In another embodiment, the present disclosure provides a method of improving at least one of muscle performance or muscle recovery from exercise. The method comprises administering to an individual performing the exercise an effective amount of a combination of at least one glycine or functional derivative thereof, at least one N-acetylcysteine or functional derivative thereof, and at least one nicotinamide riboside or NAD$^+$ precursor during at least one time selected from the group consisting of before the exercise, during the exercise, and after the exercise.

In another embodiment, the present disclosure provides a composition comprising a combination of at least one glycine or functional derivative thereof, at least one N-acetylcysteine or functional derivative thereof, and at least one nicotinamide riboside or NAD$^+$ precursor. The composition can also comprise a combination of at least one glycine or functional derivative thereof and at least one nicotinamide riboside or NAD$^+$ precursor. The composition can also comprise a combination of at least one N-acetylcysteine or functional derivative thereof, and at least one nicotinamide riboside or NAD$^+$ precursor.

The composition comprises the combination in an amount effective for at least one of (i) treating or preventing at least one physical state selected from the group consisting of oxidative stress, a condition associated with oxidative stress, a reduced level of glutathione, a condition associated with a reduced level of glutathione, or (ii) improving one or more of fetal metabolic programming for prevention of later development of obesity, pre-diabetes and/or diabetes, maternal and fetal health in gestational diabetes, exercise capacity and physical function, quality of life, longevity, memory, cognition, post-traumatic recovery and survival, or recovery from trauma and surgery.

In an embodiment, the amount of the combination is effective to treat or prevent at least one physical state selected from the group consisting of deleterious effects of aging, muscle loss, pre-diabetes, gestational diabetes, type I diabetes, type II diabetes, complications from diabetes, insulin resistance, metabolic syndrome, dyslipidemia, overweight, obesity, raised cholesterol levels, raised triglyceride levels, elevated fatty acid levels, fatty liver disease, renal disease, cardiovascular disease, neurodegenerative disease, impaired cognitive function, myopathy such as statin-induced myopathy, non-alcoholic steatohepatitis, tinnitus, dizziness, alcohol hangover, hearing impairment, osteoporosis, hypertension, atherosclerosis/coronary artery disease, myocardial damage after stress, traumatic brain injury, cystic fibrosis, inflammation, cancer, and HIV infection.

In an embodiment, the composition is selected from the group consisting of a food product, a food for special medical purposes (FSMP), a nutritional supplement, a ready to drink formula, a dairy-based drink, a low-volume liquid supplement, powder formats for liquid reconstitution, a meal replacement beverage, and combinations thereof.

In another embodiment, the present disclosure provides a method of achieving at least one result selected from the group consisting of (i) reducing severity and/or incidence of effects of aging, (ii) maintaining or improving cellular functioning and/or overall health, (iii) supporting at least one of normal mitochondrial function, cellular protection, or energy metabolism, (iv) increasing daily energy level, (v) reducing fatigue, (vi) maintaining or improving physical energy and/or cognitive performance, (vii) promoting healthy aging by promoting healthy or normal cellular function, (viii) supporting healthy skin, (ix) treating heat failure and/or reducing severity or incidence of heart failure, (x) treating, reducing incidence of, or reducing severity of oxidative stress and/or reduced glutathione (GSH) experienced during a time period comprising a stay in an intensive care unit (ICU), (xi) treating, reducing incidence of, or reducing severity of another condition associated with oxidative stress and/or reduced GSH, (xii) promoting rehabilitation from injury, illness or surgery, (xiii) modulating NAD$^+$ levels in a patient having cancer or in remission from cancer, (xiv) treating, reducing incidence of, or reducing severity of symptoms from bariatric surgery, (xv) treating, reducing incidence of, or reducing severity of non-alcoholic fatty liver disease (NAFLD), (xvi) treating, reducing incidence of, or reducing severity of human immunodeficiency virus infection (HIV), and (xvii) combinations thereof, the method comprising administering to an individual an effective amount of a combination of at least one glycine or functional derivative thereof, at least one N-acetylcysteine or functional derivative thereof, and at least one nicotinamide riboside or NAD$^+$ precursor.

In another embodiment, the present disclosure provides a composition comprising a combination of at least one glycine or functional derivative thereof, at least one N-acetylcysteine or functional derivative thereof, and at least one nicotinamide riboside or NAD$^+$ precursor, the composition comprises the combination in an amount effective for at least one of (i) reducing severity and/or incidence of effects of aging, (ii) maintaining or improving cellular functioning and/or overall health, (iii) supporting at least one of normal mitochondrial function, cellular protection, or energy metabolism, (iv) increasing daily energy level, (v) reducing fatigue, (vi) maintaining or improving physical energy and/or cognitive performance, (vii) promoting healthy aging by promoting healthy or normal cellular function, (viii) supporting healthy skin, (ix) treating heat failure and/or reducing severity or incidence of heart failure, (x) treating, reducing incidence of, or reducing severity of oxidative stress and/or reduced glutathione (GSH) experienced during a time period comprising a stay in an intensive care unit (ICU), (xi) treating, reducing incidence of, or reducing severity of another condition associated with oxidative stress and/or reduced GSH, (xii) promoting rehabilitation from injury, illness or surgery, (xiii) modulating NAD$^+$ levels in a patient having cancer or in remission from cancer, (xiv)

treating, reducing incidence of, or reducing severity of symptoms from bariatric surgery, (xv) treating, reducing incidence of, or reducing severity of non-alcoholic fatty liver disease (NAFLD), or (xvi) treating, reducing incidence of, or reducing severity of human immunodeficiency virus infection (HIV).

An advantage of one or more embodiments provided by the present disclosure is to potentiate benefits on oxidative metabolism and prevent DNA damage.

Another advantage of one or more embodiments provided by the present disclosure is to replenish $NAD^+$ pools, which decline with age.

Yet another advantage of one or more embodiments provided by the present disclosure is to help off-set slowing of the metabolism associated with aging.

Another advantage of one or more embodiments provided by the present disclosure is to help increase fatty acids metabolism.

An advantage of one or more embodiments provided by the present disclosure is to help maintain heart health, treat heat failure, and/or reduce severity or incidence of heart failure.

Another advantage of one or more embodiments provided by the present disclosure is to help support healthy LDL-cholesterol and fatty acid levels in the blood.

Yet another advantage of one or more embodiments provided by the present disclosure is to supplement key amino acids which become less available in cells in sufficient quantities during aging.

An advantage of one or more embodiments provided by the present disclosure is to provide amino acids that are precursors to the production of Glutathione, which is important for cellular function.

Another advantage of one or more embodiments provided by the present disclosure is to help increase Glutathione levels within cells.

Yet another advantage of one or more embodiments provided by the present disclosure is to improve concentration of Glutathione levels which decline with age.

An advantage of one or more embodiments provided by the present disclosure is to help maintain healthy muscle mass.

Another advantage of one or more embodiments provided by the present disclosure is to help reduce oxidative stress on the body.

Yet another advantage of one or more embodiments provided by the present disclosure is to support a normal immune system via Glutathione modulation.

Additional features and advantages are described herein and will be apparent from the following FIGURES and Detailed Description.

BRIEF DESCRIPTION OF DRAWINGS

FIG. 1 is graph of data from the experimental example disclosed herein.

FIG. 1. Effect of the combination of NAC, glycine and NR on the mitochondrial respiration. High-resolution respirometry of isolated mitochondria from muscle of adult zebrafish (N=5-6/condition). Acute oxidative stress was induced with a 2 h-treatment with menadione (Men). Rescue of the respiration was assessed with a treatment of 2 h with low doses of NAC+glycine (glyNAC; NAC 100 uM, glycine 100 uM) and low dose of NR (50 uM). Data of respiration measurements are shown in 1A. Theoretical additive effect (ΔglyNAC+ΔNR) has been calculated as the sum of the mean of glyNAC and NR and have been compared to the synergistic effect (ΔglyNAC+NR) (1B). Men=menadione control; NAC=N-acetylcysteine; gly=glycine, NR=Nicotinamide riboside. *$p<0.05$, $p<0.01$, **$p<0.0001$

DETAILED DESCRIPTION

Definitions

Some definitions are provided hereafter. Nevertheless, definitions may be located in the "Embodiments" section below, and the above header "Definitions" does not mean that such disclosures in the "Embodiments" section are not definitions.

All percentages expressed herein are by weight of the total weight of the composition unless expressed otherwise. As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified. A composition "consisting essentially of" contains at least 50 wt. % of the referenced components, preferably at least 75 wt. % of the referenced components, more preferably at least 85 wt. % of the referenced components, most preferably at least 95 wt. % of the referenced components.

The term "and/or" used in the context of "X and/or Y" should be interpreted as "X," or "Y," or "X and Y." Similarly, "at least one of X or Y" should be interpreted as "X," or "Y," or "X and Y." For example, "at least one glycine or a functional derivative thereof" should be interpreted as "glycine," or "a functional derivative of glycine," or "both glycine and a functional derivative of glycine."

Where used herein, the terms "example" and "such as," particularly when followed by a listing of terms, are merely exemplary and illustrative and should not be deemed to be exclusive or comprehensive. As used herein, a condition "associated with" or "linked with" another condition means the conditions occur concurrently, preferably means that the conditions are caused by the same underlying condition, and most preferably means that one of the identified conditions is caused by the other identified condition.

The terms "food," "food product" and "food composition" mean a product or composition that is intended for ingestion by an individual such as a human and provides at least one nutrient to the individual. A food product typically includes at least one of a protein, a lipid, a carbohydrate and optionally includes one or more vitamins and minerals. The compositions of the present disclosure, including the many embodiments described herein, can comprise, consist of, or consist essentially of the elements disclosed herein, as well as any additional or optional ingredients, components, or elements described herein or otherwise useful in a diet.

As used herein, the term "isolated" means removed from one or more other compounds or components with which the compound may otherwise be found, for example as found in nature. For example, "isolated" preferably means that the identified compound is separated from at least a portion of the cellular material with which it is typically found in nature. In an embodiment, an isolated compound is pure, i.e., free from any other compound.

"Prevention" includes reduction of risk and/or severity of a condition or disorder. The terms "treatment," "treat" and "to alleviate" include both prophylactic or preventive treatment (that prevent and/or slow the development of a targeted pathological condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition. A treatment can be patient- or doctor-related.

The term "unit dosage form", as used herein, refers to physically discrete units suitable as unitary dosages for human and animal subjects, each unit containing a predetermined quantity of the composition disclosed herein in an amount sufficient to produce the desired effect, in association with a pharmaceutically acceptable diluent, carrier or vehicle. The specifications for the unit dosage form depend on the particular compounds employed, the effect to be achieved, and the pharmacodynamics associated with each compound in the host.

A "subject" or "individual" is a mammal, preferably a human. The term "elderly" in the context of a human means an age from birth of at least 60 years, preferably above 63 years, more preferably above 65 years, and most preferably above 70 years. The term "older adult" in the context of a human means an age from birth of at least 45 years, preferably above 50 years, more preferably above 55 years, and includes elderly individuals.

As used herein, an "effective amount" is an amount that prevents a deficiency, treats a disease or medical condition in an individual, or, more generally, reduces symptoms, manages progression of the disease, or provides a nutritional, physiological, or medical benefit to the individual. The relative terms "improved," "increased," "enhanced" and the like refer to the effects of the composition disclosed herein, namely a composition comprising at least one glycine or functional derivative thereof, at least one N-acetylcysteine or functional derivative thereof, and at least one nicotinamide riboside or $NAD^+$ precursor, relative to a composition lacking at least one glycine or functional derivative thereof, at least one N-acetylcysteine or functional derivative thereof, and at least one nicotinamide riboside or $NAD^+$ precursor but otherwise identical. As used herein, "promoting" refers to enhancing or inducing relative to the level before administration of the composition disclosed herein.

"Sarcopenia" is defined as the age-associated loss of muscle mass and functionality (including muscle strength and gait speed). As used herein, "frailty" is defined as a clinically recognizable state of increased vulnerability resulting from aging-associated decline in reserve and function across multiple physiologic systems such that the ability to cope with everyday or acute stressors is compromised. In the absence of an established quantitative standard, frailty has been operationally defined by Fried et al. as meeting three out of five phenotypic criteria indicating compromised energetics: (1) weakness (grip strength in the lowest 20% of population at baseline, adjusted for gender and body mass index), (2) poor endurance and energy (self-reported exhaustion associated with $VO_2$ max), (3) slowness (lowest 20% of population at baseline, based on time to walk 15 feet, adjusting for gender and standing height), (4) low physical activity (weighted score of kilocalories expended per week at baseline, lowest quintile of physical activity identified for each gender; e.g., less than 383 kcal/week for males and less than 270 kcal/week for females), and/or unintentional weight loss (10 lbs. in past year). Fried L P, Tangen C M, Walston J, et al., "Frailty in older adults: evidence for a phenotype." J. Gerontol. A. Biol. Sci. Med. Sci. 56(3): M146-M156 (2001). A pre-frail stage, in which one or two of these criteria are present, identifies a high risk of progressing to frailty.

"Cachexia" is a severe body wasting condition characterized by marked weight loss, anorexia, asthenia, and anaemia. Cachexia is a common feature of a number of illnesses, such as cancer, sepsis, chronic heart failure, rheumatoid arthritis, and acquired immune deficiency syndrome (AIDS).

"Overweight" is defined for a human as a body mass index (BMI) between 25 and 30 $kg/m^2$. "Obese" is defined for a human as a BMI of at least 30 $kg/m^2$, for example 30-39.9 $kg/m^2$. "Weight loss" is a reduction of the total body weight. Weight loss may, for example, refer to the loss of total body mass in an effort to improve one or more of health, fitness or appearance.

"Diabetes" encompasses both the type I and type II forms of the disease. Non-limiting examples of risk factors for diabetes include: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

As used herein, the term "metabolic syndrome" refers to a combination of medical disorders that, when occurring together, increase the risk of developing cardiovascular disease and diabetes. It affects one in five people in the United States and prevalence increases with age. Some studies have shown the prevalence in the United States to be an estimated 25% of the population. In accordance with the International Diabetes Foundation consensus worldwide definition (2006), metabolic syndrome is central obesity plus any two of the following:

Raised triglycerides: >150 mg/dL (1.7 mmol/L), or specific treatment for this lipid abnormality;

Reduced HDL cholesterol: <40 mg/dL (1.03 mmol/L) in males, <50 mg/dL (1.29 mmol/L) in females, or specific treatment for this lipid abnormality;

Raised blood pressure: systolic BP>130 or diastolic BP>85 mm Hg, or treatment of previously diagnosed hypertension; and Raised fasting plasma glucose: (FPG)>100 mg/dL (5.6 mmol/L), or previously diagnosed type 2 diabetes.

As used herein, "neurodegenerative disease" or "neurodegenerative disorder" refers to any condition involving progressive loss of functional neurons in the central nervous system. In an embodiment, the neurodegenerative disease is associated with age-related cell death. Non-limiting examples of neurodegenerative diseases include Alzheimer's disease, Parkinson's disease, Huntington's disease, amyotrophic lateral sclerosis (also known as ALS and as Lou Gehrig's disease), AIDS dementia complex, adrenoleukodystrophy, Alexander disease, Alper's disease, ataxia telangiectasia, Batten disease, bovine spongiform encephalopathy (BSE), Canavan disease, corticobasal degeneration, Creutzfeldt-Jakob disease, dementia with Lewy bodies, fatal familial insomnia, frontotemporal lobar degeneration, Kennedy's disease, Krabbe disease, Lyme disease, Machado-Joseph disease, multiple sclerosis, multiple system atrophy, neuroacanthocytosis, Niemann-Pick disease, Pick's disease, primary lateral sclerosis, progressive supranuclear palsy, Refsum disease, Sandhoff disease, diffuse myelinoclastic sclerosis, spinocerebellar ataxia, subacute combined degeneration of spinal cord, tabes dorsalis, Tay-Sachs disease, toxic encephalopathy, transmissible spongiform encephalopathy, and wobbly hedgehog syndrome.

As used herein, "cognitive performance" refers to how well a subject performs one or more cognitive function. As used herein, "cognitive function" refers to any mental process by which one becomes aware of, perceives, or comprehends ideas. It involves all aspects of perception, thinking, reasoning, and remembering and includes, for example, perception, memory, attention, speech comprehension, speech generation, reading comprehension, creation of imagery, learning, and reasoning. Ordinarily it will refer to at least memory.

Methods for measuring cognitive function are well-known and can include, for example, individual or battery tests for any aspect of cognitive function. One such test is the Prudhoe Cognitive Function Test by Margallo-Lana et al. (2003) J. Intellect. Disability Res. 47:488-492. Another such test is the Mini Mental State Exam (MMSE), which is designed to assess orientation to time and place, registration, attention and calculation, recall, language use and comprehension, repetition, and complex commands. Folstein et al. (1975) J. Psych. Res. 12:189-198. Other tests useful for measuring cognitive function include the Alzheimer Disease Assessment Scale-Cognitive (ADAS-Cog) (Rosen et al. (1984) Am. J. Psychiatry. 141(11):1356-64) and the Cambridge Neuropsychological Test Automated Battery (CANTAB) (Robbins et al. (1994) Dementia. 5(5):266-81). Such tests can be used to assess cognitive function in an objective manner, so that changes in cognitive function, for example in response to treatment in accordance with methods disclosed herein, can be measured and compared.

As used herein, a "cognitive disorder" refers to any condition that impairs cognitive function. Non-limiting examples of a cognitive disorder include delirium, dementia, learning disorder, attention deficit disorder (ADD), and attention deficit hyperactivity disorder (ADHD).

EMBODIMENTS

The present disclosure provides compositions comprising a combination of at least one glycine or functional derivative thereof, at least one N-acetylcysteine or functional derivative thereof, and at least one nicotinamide riboside or $NAD^+$ precursor. As used herein, "nicotinamide riboside" includes L-valine and L-phenylalanine esters of nicotinamide riboside. Non-limiting examples of suitable $NAD^+$ precursors include Tryptophan, Nicotinic Acid, Nicotinamide, reduced form of nicotinamide riboside (NRH), Nicotinamide Mononucleotide (NMN), Trigonelline, Nicotinic acid mononucleotide, Nicotinic acid riboside, and mixtures thereof. The present disclosure is not limited to a specific embodiment of the $NAD^+$ precursor, and the $NAD^+$ precursor can be any compound that stimulates $NAD^+$.

Each of the compounds can be administered at the same time as the other compounds (i.e., as a single unit) or separated by a time interval (i.e., in separate units). The present disclosure further provides a kit comprising at least one glycine or functional derivative thereof, at least one N-acetylcysteine or functional derivative thereof, and at least one nicotinamide riboside or $NAD^+$ precursor for admixing to form one or more of the compositions disclosed herein and/or for use in one or more of the methods disclosed herein, for example in separate containers as two or more liquid solutions or dried powders. In some embodiments, one or more of these compounds can be isolated compounds.

The combination of at least one glycine or functional derivative thereof and at least one N-acetylcysteine or functional derivative thereof can be provided by any of the compositions disclosed by U.S. Pat. Nos. 8,362,080, 8,802,730 and 9,084,760, each entitled "Increasing glutathione levels for therapy," and WO2016/191468 entitled "Benefits of Supplementation with N-Acetylcysteine and Glycine to Improve Glutathione Levels," each incorporated herein by reference in its entirety.

The nicotinamide riboside can be provided by any of the compositions disclosed by U.S. Pat. Nos. 8,383,086 and 8,197,807, each entitled "Nicotinamide riboside kinase compositions and methods for using the same," and U.S. Pat. No. 8,106,184 entitled "Nicotinoyl riboside compositions and methods of use," each incorporated herein by reference in its entirety.

Accordingly, an aspect of the present disclosure is a composition comprising at least one glycine or functional derivative thereof, at least one N-acetylcysteine or functional derivative thereof, and at least one nicotinamide riboside or $NAD^+$ precursor in an amount effective for treatment or prevention of at least condition selected from the group consisting of deleterious effects of aging, muscle loss (for any reason, including at least sarcopenia, HIV infection, aging, cachexia, deleterious effects of weightlessness), pre-diabetes, gestational diabetes, diabetes (type I or type II), complications from diabetes (e.g., diabetic dyslipidemia and/or diabetic microvascular complications such as nephropathy, retinopathy, and/or neuropathy), insulin resistance, metabolic syndrome, dyslipidemia, overweight, obesity, raised cholesterol levels, raised triglyceride levels, elevated fatty acid levels, fatty liver disease (e.g., non-alcoholic fatty liver disease, including with or without inflammation), renal disease, cardiovascular disease (e.g., heart failure and/or impaired cardiac contractile function, for example by treating heat failure and/or reducing severity or incidence of heart failure), neurodegenerative disease (e.g., from aging), impaired cognitive function, myopathy such as statin-induced myopathy, non-alcoholic steatohepatitis, tinnitus, dizziness, alcohol hangover, hearing impairment, osteoporosis, hypertension, atherosclerosis/coronary artery disease, myocardial damage after stress (e.g., from burns or trauma), traumatic brain injury (including concussions), cystic fibrosis, inflammation, cancer, and HIV infection. Further regarding aging, it is notable that reduction of NAD+ and glutathione can accompany aging. Further regarding cardiovascular disease (CVD), it is notable that increased homocysteine is a validated risk factor for CVD.

Another aspect of the present disclosure is a method of treating at least one of these conditions, the method comprising administering to the individual a composition comprising a therapeutically effective amount of a combination of at least one glycine or functional derivative thereof, at least one N-acetylcysteine or functional derivative thereof, and at least one nicotinamide riboside or $NAD^+$ precursor. Another aspect of the present disclosure is a method of preventing at least one of these conditions, the method comprising administering to an individual at risk of the at least one condition a composition comprising a prophylactically effective amount of a combination of at least one glycine or functional derivative thereof, at least one N-acetylcysteine or functional derivative thereof, and at least one nicotinamide riboside or $NAD^+$ precursor.

The composition can treat or prevent sarcopenia, sarcopenic obesity, or cachexia, for example cachexia from an underlying medical condition such as chronic illness, HIV, cancer, chronic obstructive pulmonary disease (COPD), and/or aging in otherwise healthy individuals. In this regard, aging can be accompanied by reduction of NAD+ and glutathione (GSH).

The composition can treat or prevent an eye condition resulting directly or indirectly from low GSH levels, including low levels in the lens of the eye that is known for being rich in glutathione. Non-limiting examples of such conditions include cataracts and/or glaucoma, presbyopia (loss of near vision with aging requiring reading glasses), and presbyacusis (loss of hearing with aging, which requires a hearing aid).

In an embodiment, the composition improves at least one of muscle performance or muscle recovery, such as from muscle stress, including muscle stress associated with exercise. The exercise may be of any kind, including aerobic ("cardio") exercise and/or weight training, for example. The composition can be administered during at least one time selected from the group consisting of before the exercise (e.g., less than one hour before), during the exercise, and after the exercise (e.g., less than one hour after the exercise).

Yet another aspect of the present disclosure is a method of delaying off-set of metabolic decline, maintaining muscle mass, decreasing oxidative stress, maintaining immune function and/or maintaining cognitive function in a healthy older adult. The method comprises administering to the healthy older adult an effective amount of a combination of at least one glycine or functional derivative thereof, at least one N-acetylcysteine or functional derivative thereof, and at least one nicotinamide riboside or $NAD^+$ precursor.

Another aspect of the present disclosure is a method of improving mitochondrial function in an individual with sarcopenia. The method comprises administering to the individual an effective amount of a combination of at least one glycine or functional derivative thereof, at least one N-acetylcysteine or functional derivative thereof, and at least one nicotinamide riboside or $NAD^+$ precursor.

Yet another aspect of the present disclosure is a method of enhancing metabolizing of reactive oxygen species, improving glucose control and/or improving muscle function in an individual with at least one of obesity, pre-diabetes or diabetes. The method comprises administering to the individual an effective amount of a combination of at least one glycine or functional derivative thereof, at least one N-acetylcysteine or functional derivative thereof, and at least one nicotinamide riboside or $NAD^+$ precursor.

Another aspect of the present disclosure is a method of improving mitochondrial function (preferably to benefit at least one of metabolism or strength) in an individual with sarcopenia. The method comprises administering to the individual an effective amount of a combination of at least one glycine or functional derivative thereof, at least one N-acetylcysteine or functional derivative thereof, and at least one nicotinamide riboside or $NAD^+$ precursor.

In another aspect, the present disclosure provides a method of improving cognitive function. The method comprises administering to an individual an effective amount of a combination of at least one glycine or functional derivative thereof, at least one N-acetylcysteine or functional derivative thereof, and at least one nicotinamide riboside or $NAD^+$ precursor. The cognitive function can be selected from the group consisting of perception, memory, attention, speech comprehension, speech generation, reading comprehension, creation of imagery, learning, reasoning, and combinations thereof. In an embodiment, the individual does not have a cognitive disorder; alternatively, the individual has a cognitive disorder. The individual can be elderly and/or can have cognitive decline associated with aging.

Yet another aspect of the present disclosure is a method of improving one or more of fetal metabolic programming for prevention of later development of obesity, pre-diabetes and/or diabetes, maternal and fetal health in gestational diabetes, exercise capacity and physical function, quality of life, longevity, memory, cognition, post-traumatic recovery and survival (e.g., post-surgical, post-sepsis, post-blunt or penetrating trauma due to accident or physical assault), or recovery from trauma and surgery. The method comprises administering to the individual an effective amount of a combination of at least one glycine or functional derivative thereof, at least one N-acetylcysteine or functional derivative thereof, and at least one nicotinamide riboside or $NAD^+$ precursor.

In another aspect, the present disclosure provides a method of achieving at least one result selected from the group consisting of (i) reducing severity and/or incidence of effects of aging, (ii) maintaining or improving cellular functioning and/or overall health, (iii) supporting at least one of normal mitochondrial function, cellular protection, or energy metabolism, (iv) increasing daily energy level, (v) reducing fatigue, (vi) maintaining or improving physical energy and/or cognitive performance, (vii) promoting healthy aging by promoting healthy or normal cellular function, (viii) supporting healthy skin, (ix) treating heat failure and/or reducing severity or incidence of heart failure, (x) treating, reducing incidence of, or reducing severity of oxidative stress and/or reduced glutathione (GSH) experienced during a time period comprising a stay in an intensive care unit (ICU), (xi) treating, reducing incidence of, or reducing severity of another condition associated with oxidative stress and/or reduced GSH, (xii) promoting rehabilitation from injury, illness or surgery, for example rehabilitation specific to neurological conditions such as traumatic brain injury or stroke, (xiii) modulating NAD+ levels in a patient having cancer or in remission from cancer, (xiv) treating, reducing incidence of, or reducing severity of symptoms from bariatric surgery, (xv) treating, reducing incidence of, or reducing severity of non-alcoholic fatty liver disease (NAFLD), (xvi) treating, reducing incidence of, or reducing severity of human immunodeficiency virus infection (HIV), and (xvii) combinations thereof, the method comprising administering to an individual an effective amount of a combination of at least one glycine or functional derivative thereof, at least one N-acetylcysteine or functional derivative thereof, and at least one nicotinamide riboside or NAD+ precursor.

A particularly preferred embodiment is a method of treating, reducing incidence of, or reducing severity of at least one condition selected from the group consisting of metabolic syndrome, age-related decline in metabolic regulation, and muscle indications, the method comprising administering to an individual in need thereof or at risk thereof an effective amount of a combination of at least one glycine or functional derivative thereof, at least one N-acetylcysteine or functional derivative thereof, and at least one nicotinamide riboside or NAD+ precursor.

In each of the compositions and methods disclosed herein, the composition is preferably a food product, including food additives, food ingredients, functional foods, dietary supplements, medical foods, nutraceuticals, or food supplements. For example, the composition can be selected from the group consisting of a food product, a food for special medical purposes (FSMP), a nutritional supplement, a ready to drink formula, a dairy-based drink, a low-volume liquid supplement (i.e., about 50 ml or less, for example about 30 ml or less), powder formats for liquid reconstitution, a meal replacement beverage, and combinations thereof.

As used herein, a "functional derivative" of glycine is a glycine functional derivative that is effective in an individual in conjunction with N-acetylcysteine or a functional derivative thereof to increase intracellular GSH levels. A "functional derivative" of N-acetylcysteine is an N-acetylcysteine functional derivative that is effective in an individual in by itself or in conjunction with glycine (or a functional derivative thereof) to increase intracellular GSH levels.

The glycine is preferably L-glycine and/or L-glycine ethyl ester. Non-limiting examples of suitable glycine functional derivatives include D-Allylglycine; N-[Bis(methylthio)methylene]glycine methyl ester; Boc-allyl-Gly-OH (dicyclohexylammonium) salt; Boc-D-Chg-OH; Boc-Chg-OH; (R)-N-Boc-(2'-chlorophenyl)glycine; Boc-L-cyclopropylglycine; Boc-L-cyclopropylglycine; (R)-N-Boc-4-fluorophenylglycine; Boc-D-propargylglycine; Boc-(S)-3-thienylglycine; Boc-(R)-3-thienylglycine; D-a-Cyclohexylglycine; L-a-Cyclopropylglycine; N-(2-fluorophenyl)-N-(methylsulfonyl)glycine; N-(4-fluorophenyl)-N-(methylsulfonyl)glycine; Fmoc-N-(2,4-dimethoxybenzyl)-Gly-OH; N-(2-Furoyl)glycine; L-a-Neopentylglycine; D-Propargylglycine; sarcosine; Z-a-Phosphonoglycine trimethyl ester, and a mixture thereof. In an embodiment, both the glycine and the N-acetylcysteine may be provided in a dipeptide, such as N-acetylcysteinylglycine or cysteinylglycine.

The composition can be administered at least one day per week, preferably at least two days per week, more preferably at least three or four days per week (e.g., every other day), most preferably at least five days per week, six days per week, or seven days per week. The time period of administration can be at least one week, preferably at least one month, more preferably at least two months, most preferably at least three months, for example at least four months. In an embodiment, dosing is at least daily; for example, a subject may receive one or more doses daily. In some embodiments, the administration continues for the remaining life of the individual. In other embodiments, the administration occurs until no detectable symptoms of the medical condition remain. In specific embodiments, the administration occurs until a detectable improvement of at least one symptom occurs and, in further cases, continues to remain ameliorated.

The glycine and the N-acetylcysteine may be formulated in a particular ratio. In some embodiments, the formulation may comprise these components in the following exemplary ratios: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, 1:150, 1:200, 1:300, 1:400, 1:500, 1:600, 1:750, 1:1000, and 1:10,000. In particular embodiments, the formulation may comprise these components in the following weight percentages (either the same for both glycine and the N-acetylcysteine or different weight percentages for each): 1%, 2%, 3%, 4%, 5%, 6%, 7%, 8%, 9%, 10%, 12%, 15%, 20%, 25%, 30%, 40%, 45%, 50%, 55%, 60%, 65%, 70%, 75%, 80%, 85%, 90%, 95%, 97%, or 99%, for example.

The N-acetylcysteine or functional derivative thereof can be administered in an amount of about 0.1-100 milligram (mg) of N-acetylcysteine (NAC) or functional derivative thereof per kilogram (kg) of body weight of the subject. The glycine (GLY) or functional derivative thereof can be administered in an amount of about 0.1-100 milligram (mg) of glycine or functional derivative thereof per kilogram (kg) of body weight of the subject. In some embodiments, these amounts are provided at least partially by a dipeptide comprising both the N-acetylcysteine or functional derivative thereof and the glycine or functional derivative thereof.

In a particular non-limiting example, the daily doses for a 60 kg subject can be as follows:
NAC or derivative thereof: 6 to 6,000 mg/day
GLY or derivative thereof: 6 to 6,000 mg/day
Nicotinamide Riboside: 0.001 to 1,000 mg/day The nicotinamide riboside or NAD+ precursor can be administered in an amount of about 0.001 mg/day to about 2000 mg/day, preferably about 0.001 mg/day to about 1000 mg/day, more preferably about 0.001 mg/day to about 750 mg/day, even more preferably about 0.001 mg/day to about 500 mg/day, most preferably about 0.001 mg/day to about 250 mg/day, for example about 0.001 mg/day to about 100 mg/day, about 0.001 mg/day to about 75 mg/day, about 0.001 mg/day to about 50 mg/day, about 0.001 mg/day to about 25 mg/day, about 0.001 mg/day to about 10 mg/day, or about 0.001 mg/day to about 1 mg/day. Of course, the daily dose can be administered in portions at various hours of the day. However, in any given case, the amount of compound administered will depend on such factors as the solubility of the active component, the formulation used, subject condition (such as weight), and/or the route of administration. For example, the daily doses of nicotinamide riboside disclosed above are non-limiting and, in some embodiments, may be different; in particular, the compositions disclosed herein can be utilized as an acute care food for special medical purposes (FSMP) and contain up to about 2.0 mg nicotinamide riboside/day.

The compositions disclosed herein may be administered to the subject orally or parenterally. Non-limiting examples of parenteral administration include intravenously, intramuscularly, intraperitoneally, subcutaneously, intraarticularly, intrasynovially, intraocularly, intrathecally, topically, and inhalation. As such, non-limiting examples of the form of the composition include natural foods, processed foods, natural juices, concentrates and extracts, injectable solutions, microcapsules, nano-capsules, liposomes, plasters, inhalation forms, nose sprays, nosedrops, eyedrops, sublingual tablets, and sustained-release preparations.

The compositions disclosed herein can use any of a variety of formulations for therapeutic administration. More particularly, pharmaceutical compositions can comprise appropriate pharmaceutically acceptable carriers or diluents and may be formulated into preparations in solid, semi-solid, liquid or gaseous forms, such as tablets, capsules, powders, granules, ointments, solutions, suppositories, injections, inhalants, gels, microspheres, and aerosols. As such, administration of the composition can be achieved in various ways, including oral, buccal, rectal, parenteral, intraperitoneal, intradermal, transdermal, and intratracheal administration. The active agent may be systemic after administration or may be localized by the use of regional administration, intramural administration, or use of an implant that acts to retain the active dose at the site of implantation.

In pharmaceutical dosage forms, the compounds may be administered as their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose functional derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional, additives such as solubilizers, isotonic agents, suspending agents, emulsifying agents, stabilizers and preservatives.

The compounds can be utilized in an aerosol formulation to be administered by inhalation. For example, the compounds can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds can be administered rectally by a suppository. The suppository can include a vehicle such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition. Similarly, unit dosage forms for injection or intravenous administration may comprise the compounds in a composition as a solution in sterile water, normal saline or another pharmaceutically acceptable carrier, wherein each dosage unit, for example, mL or L, contains a predetermined amount of the composition containing one or more of the compounds.

EXAMPLE

The following non-limiting prophetic example discusses experimental data that is being investigated and/or will be investigated to further support the compounds, compositions, and methods disclosed herein.

Chronic Oxidative Stress Induces Changes in Cellular Respiratory Rate

Menadione-induced oxidative stress in HepG2 cells treated with BSO (GSH synthesis inhibitor) Seahorse measurement (repiratory rate)

Synergistic Reduction of Oxidative Stress and Oxidative Stress-Derived Effects Glycine, NAC and NR Menadione-induced oxidative stress in HepG2 cells treated with BSO (GSH synthesis inhibitor), NAC+/−glycine+/−NR_Cell growth (protein concentration)

Menadione-induced oxidative stress in HepG2 cells treated with BSO (GSH synthesis inhibitor), NAC+/−glycine+/−NR_GSH production Menadione-induced oxidative stress in HepG2 cells treated with BSO (GSH synthesis inhibitor), NAC+/−glycine+/−NR_Metabolic profiling Menadione-induced oxidative stress in HepG2 cells treated with BSO (GSH synthesis inhibitor), NAC+/−glycine+/−NR_Seahorse measurement (repiratory rate)

Menadione-induced oxidative stress in HepG2 cells treated with BSO (GSH synthesis inhibitor), NAC+/−glycine+/−NR_NAPD-NAD redox status Menadione-induced oxidative stress in Zebrafish treated with BSO (GSH synthesis inhibitor), NAC+/−glycine+/−NR_Oxidative stress measurement Menadione-induced oxidative stress in Zebrafish treated with BSO (GSH synthesis inhibitor), NAC+/−glycine+/−NR_GSH production Menadione-induced oxidative stress in Zebrafish treated with BSO (GSH synthesis inhibitor), NAC+/−glycine+/−NR_Metabolic profiling Menadione-induced oxidative stress in Zebrafish treated with BSO (GSH synthesis inhibitor), NAC+/−glycine+/−NR_Mitochondrial function (respiratory rate by Oroboros, complex activity, etc.)

Example: Combination of Low Doses of GlyNAC-NR Induce the Rescue of the Mitochondrial Respiration after Acute Oxidative Stress Material and Methods
Zebrafish
Adult AB zebrafish were raised at 28° C. under standard husbandry conditions. 4 months old fish were exposed in water to acute oxidative stress with 3 μM Menadione (Sigma-Aldrich) incubation for 2 h at 28° C. Controls of the oxidative stress were then incubated in clean water for 2 h at 28° C. Fish exposed to the treatment were incubated in water containing the compound of interest for 2 h at 28° C. The compounds used were: N-acetylcysteine (NAC) (Sigma-Aldrich); glycine (Sigma-Aldrich); nicotinamide riboside (NR) (Chromadex).

Mitochondria Isolation and High-Resolution Respirometry

Mitochondria crude extracts were prepared from fish trunk muscles as previously described, with minor changes (Frezza et al., 2007). After BCA quantification of protein concentration, 150 μg of crude extract were used for high-resolution respirometry quantification. The Oxygraph-2k (O2k, OROBOROS Instruments) was used for measurements of respiration. Up to two O2k instruments (four chambers) were used in parallel. Experiments were performed at 28° C. in modified MiR05 (110 mM sucrose, 0.5 mM EGTA, 3 mM $MgCl_2$, 20 mM taurine, 10 mM $KH_2PO_4$, 20 mM HEPES and 0.1% BSA essentially fatty acid free). Respiration of isolated mitochondria was determined using substrate-uncoupler-inhibitor titration (SUIT) protocols (Pesta and Gnaiger, 2012) with modifications. Pyruvate, glutammate and malate (5 mM, 10 mM, 2 mM, respectively) were used as substrate to induce Complex I (CI) respiration in presence of ADP (1 mM). The addition of succinate (10 mM) in presence of ADP was used to induce Complex II (CII) respiration. CI respiration was calculated as the difference between total respiration (CI+CII) and the addition of CI inhibitor rotenone (0.5 μM); CII respiration was calculated as the difference between inhibited CI respiration and the addition of CII inhibitor malonic acid (5 mM). Total respiration (CI+CII, Tot resp) was assessed as the difference of the respiration in presence of all substrates and the total inhibition of CI and CII.

Statistics

All numerical data are expressed as mean±SEM and reported as histograms. 2-way ANOVA test with Tukey post hoc test was used for statistical analysis and differences were considered statistically significant for $p<0.05$.

Results

FIG. 1 shows the effect of the combination of GlyNAC and NR on high-resolution respirometry. Fish (N=5-6/condition) were treated for 2 h with low doses of NAC (100 μM), glycine (100 μM) and NR (50 μM), and GlyNAC and NR single treatments were compared to the combination of the three compounds. The concentrations chosen do not show any significant effect when used alone. We thus show in FIG. 1A that combining low doses improve the CI respiration and total respiration significantly compared to menadione control and single compounds. In FIG. 1B, synergistic effect have been calculated as the difference between each condition and the mean of the menadione control. Theoretical additive effect (ΔGlyNAC+ΔNR) has been calculated as the sum of the means of the condition ΔGlyNAC and ΔNR. The effect of the co-treatment (ΔGlyNAC+NR) is significantly higher when compared to the single compounds (ΔGlyNAC and ΔNR), while there is a trend when compared to the additive effect (ΔGlyNAC+ΔNR) but not significant.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of treating, reducing incidence of, or reducing severity of at least one condition selected from the group consisting of metabolic syndrome, age-related decline in metabolic regulation, and muscle indications, the method comprising administering to an individual in need thereof or at risk thereof an effective amount of a combination of (1) at least one glycine or functional derivative thereof, (2) at least one N-acetylcysteine or functional derivative thereof, and (3) at least one nicotinamide riboside or $NAD^+$ precursor, wherein the individual does not have fatty liver disease (AFLD), does not have type 2 diabetes, does not have obesity, does not have insulin resistance, and does not have dyslipidemia.

2. The method of claim 1, wherein the at least one glycine or functional derivative thereof is selected from the group consisting of L-glycine, L-glycine ethyl ester, D-Allylglycine; N-[Bis(methylthio)methylene]glycine methyl ester; Boc-allyl-Gly-OH (dicyclohexylammonium) salt; Boc-D-Chg-OH; Boc-Chg-OH; (R)-N-Boc-(2'-chlorophenyl)glycine; Boc-L-cyclopropylglycine; Boc-L-cyclopropylglycine; (R)-N-Boc-4-fluorophenylglycine; Boc-D-propargylglycine; Boc-(S)-3-thienylglycine; Boc-(R)-3-thienylglycine; D-a-Cyclohexylglycine; L-a-Cyclopropylglycine; N-(2-fluorophenyl)-N-(methyl sulfonyl)glycine; N-(4-fluorophenyl)-N-(methylsulfonyl) glycine; Fmoc-N-(2,4-dimethoxybenzyl)-Gly-OH; N-(2-Furoyl)glycine; L-a-Neopentylglycine; D-Propargylglycine; sarcosine; Z-a-Phosphonoglycine trimethyl ester, and mixtures thereof.

3. The method of claim 1, wherein the combination is administered orally.

4. The method of claim 1, wherein the combination is administered in a composition selected from the group consisting of a food product, a food for special medical purposes (FSMP), a nutritional supplement, a ready to drink formula, a dairy-based drink, a low-volume liquid supplement, powder formats for liquid reconstitution, a meal replacement beverage, and combinations thereof.

5. The method of claim 1, wherein the combination is administered in a composition that comprises a dipeptide that provides at least a portion of the at least one glycine or functional derivative thereof and the at least one N-acetylcysteine or functional derivative thereof.

6. The method of claim 1, wherein (1) the at least one glycine or functional derivative thereof, (2) the at least one N-acetylcysteine or functional derivative thereof, and (3) the at least one nicotinamide riboside or $NAD^+$ precursor are administered in the same composition.

7. The method of claim 1, wherein one or more of (1) the at least one glycine or functional derivative thereof, (2) the at least one N-acetylcysteine or functional derivative thereof, and (3) the at least one nicotinamide riboside or $NAD^+$ precursor are administered in a different composition relative to the remainder of the combination.

8. The method of claim 1, wherein the $NAD^+$ precursor is selected from the group consisting of Tryptophan, Nicotinic Acid, Nicotinamide, reduced form of nicotinamide riboside (NRH), Nicotinamide Mononucleotide (NMN) Trigonelline, Nicotinic acid mononucleotide, Nicotinic acid riboside, and mixtures thereof.

9. A method of treating or preventing at least one physical state selected from the group consisting of oxidative stress, a condition associated with oxidative stress, a reduced level of glutathione, and a condition associated with a reduced level of glutathione, the method comprising administering to an individual in need thereof an effective amount of a combination of (1) at least one glycine or functional derivative thereof, (2) at least one N-acetylcysteine or functional derivative thereof, and (3) at least one nicotinamide riboside or $NAD^+$ precursor, wherein the individual does not have fatty liver disease (AFLD), does not have type 2 diabetes, does not have obesity, does not have insulin resistance, and does not have dyslipidemia.

10. The method of claim 9, wherein the at least one physical state is selected from the group consisting of deleterious effects of aging, muscle loss, pre-diabetes, gestational diabetes, type I diabetes, complications from diabetes, metabolic syndrome, overweight, raised cholesterol levels, raised triglyceride levels, elevated fatty acid levels, renal disease, cardiovascular disease, neurodegenerative disease, impaired cognitive function, myopathy, non-alcoholic steatohepatitis, tinnitus, dizziness, alcohol hangover, hearing impairment, osteoporosis, hypertension, atherosclerosis/coronary artery disease, myocardial damage after stress, traumatic brain injury, cystic fibrosis, inflammation, cancer, and HIV infection.

11. The method of claim 9, wherein the at least one glycine or functional derivative thereof is selected from the group consisting of L-glycine, L-glycine ethyl ester, D-Allylglycine; N-[Bis(methylthio)methylene]glycine methyl ester; Boc-allyl-Gly-OH (dicyclohexylammonium) salt; Boc-D-Chg-OH; Boc-Chg-OH; (R)-N-Boc-(2'-chlorophenyl)glycine; Boc-L-cyclopropylglycine; Boc-L-cyclopropylglycine; (R)-N-Boc-4-fluorophenylglycine; Boc-D-propargylglycine; Boc-(S)-3-thienylglycine; Boc-(R)-3-thienylglycine; D-a-Cyclohexylglycine; L-a-Cyclopropylglycine; N-(2-fluorophenyl)-N-(methyl sulfonyl)glycine; N-(4-fluorophenyl)-N-(methylsulfonyl) glycine; Fmoc-N-(2,4-dimethoxybenzyl)-Gly-OH; N-(2-Furoyl)glycine; L-a-Neopentylglycine; D-Propargylglycine; sarcosine; Z-a-Phosphonoglycine trimethyl ester, and mixtures thereof.

12. The method of claim 9, wherein the combination is administered orally.

13. The method of claim 9, wherein the combination is administered in a composition selected from the group consisting of a food product, a food for special medical purposes (FSMP), a nutritional supplement, a ready to drink formula, a dairy-based drink, a low-volume liquid supplement, powder formats for liquid reconstitution, a meal replacement beverage, and combinations thereof.

14. The method of claim 9, wherein the combination is administered in a composition that comprises a dipeptide that provides at least a portion of the at least one glycine or functional derivative thereof and the at least one N-acetylcysteine or functional derivative thereof.

15. The method of claim 9, wherein (1) the at least one glycine or functional derivative thereof, (2) the at least one N-acetylcysteine or functional derivative thereof, and (3) the at least one nicotinamide riboside or NAD$^+$ precursor are administered in the same composition.

16. The method of claim 9, wherein one or more of (1) the at least one glycine or functional derivative thereof, (2) the at least one N-acetylcysteine or functional derivative thereof, and (3) the at least one nicotinamide riboside or NAD$^+$ precursor are administered in a different composition relative to the remainder of the combination.

17. A method of delaying off-set of metabolic decline, maintaining muscle mass, decreasing oxidative stress, maintaining immune function and/or maintaining cognitive function in a healthy older adult, the method comprising administering to the healthy older adult an effective amount of a combination of (1) at least one glycine or functional derivative thereof, (2) at least one N-acetylcysteine or functional derivative thereof, and (3) at least one nicotinamide riboside or NAD$^+$ precursor,
wherein the healthy older adult does not have fatty liver disease (AFLD), does not have type 2 diabetes, does not have obesity, does not have insulin resistance, and does not have dyslipidemia.

18. The method of claim 17, wherein the healthy older adult is elderly.

19. The method of claim 10, wherein the myopathy is statin-induced myopathy.

* * * * *